US009662509B2

United States Patent
Lapid et al.

(10) Patent No.: US 9,662,509 B2
(45) Date of Patent: May 30, 2017

(54) INTRALUMINAL ACTIVATION SYSTEM AND METHOD OF ACTIVATING AN INACTIVE AGENT

(71) Applicant: Cook Medical Technologies LLC, Bloomington, IN (US)

(72) Inventors: Inbal Sarah Lapid, Bloomington, IN (US); Adam Brian McCullough, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 558 days.

(21) Appl. No.: 14/197,626

(22) Filed: Mar. 5, 2014

(65) Prior Publication Data

US 2014/0350455 A1 Nov. 27, 2014

Related U.S. Application Data

(60) Provisional application No. 61/826,536, filed on May 23, 2013.

(51) Int. Cl.
*A61N 5/06* (2006.01)
*A61M 25/10* (2013.01)

(52) U.S. Cl.
CPC ....... *A61N 5/062* (2013.01); *A61M 2025/105* (2013.01); *A61N 2005/0602* (2013.01); *A61N 2005/063* (2013.01)

(58) Field of Classification Search
CPC ..... A61M 2025/105; A61N 2005/0602; A61N 2005/063; A61N 5/062
See application file for complete search history.

(56) References Cited

U.S. PATENT DOCUMENTS

| | | |
|---|---|---|
| 5,800,478 A | 9/1998 | Chen et al. |
| 7,018,395 B2 | 3/2006 | Chen |
| 2004/0202692 A1 | 10/2004 | Shanley et al. |
| 2005/0228260 A1 | 10/2005 | Burwell et al. |
| 2009/0118816 A1 | 5/2009 | Kipshidze et al. |
| 2009/0275878 A1 | 11/2009 | Cambier et al. |
| 2010/0249912 A1 | 9/2010 | Gibbons, Jr. et al. |
| 2012/0303011 A1* | 11/2012 | Schaeffer ............... A61B 18/24 606/16 |

* cited by examiner

*Primary Examiner* — Imani Hayman
(74) *Attorney, Agent, or Firm* — Liell & McNeil

(57) ABSTRACT

An intraluminal activation system for activating an inactive agent includes a catheter defining an inflation lumen and a medical device lumen. A longitudinal distal segment of the catheter defines a transparent treatment region. An inflation balloon is disposed at the distal end of the catheter and over at least a portion of the transparent treatment region. An elongate energy transmission wire is configured to transmit activation energy from a proximal end thereof to a distal end thereof. The activation system has a configuration in which the balloon is expanded, the energy transmission wire is received within the medical device lumen such that the distal end of the energy transmission wire is within the transparent treatment region, and activation energy is emitted from the energy transmission wire, through the transparent treatment region, through the balloon, and toward the inactive agent.

20 Claims, 3 Drawing Sheets

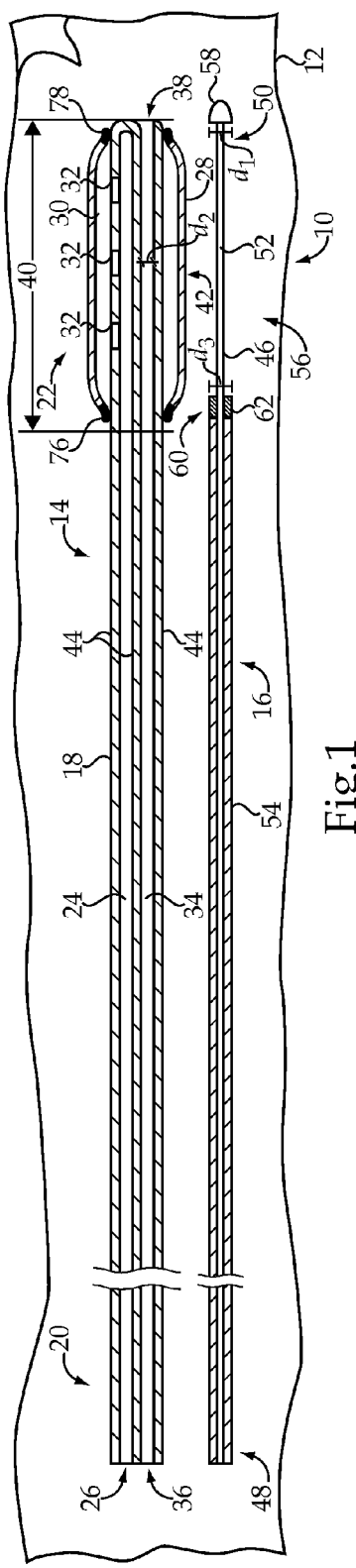
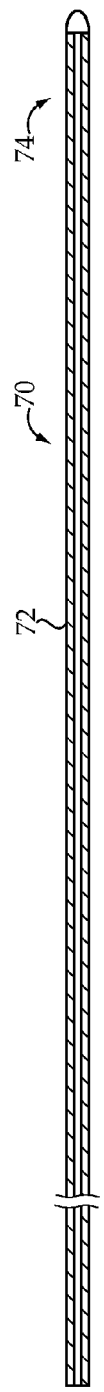
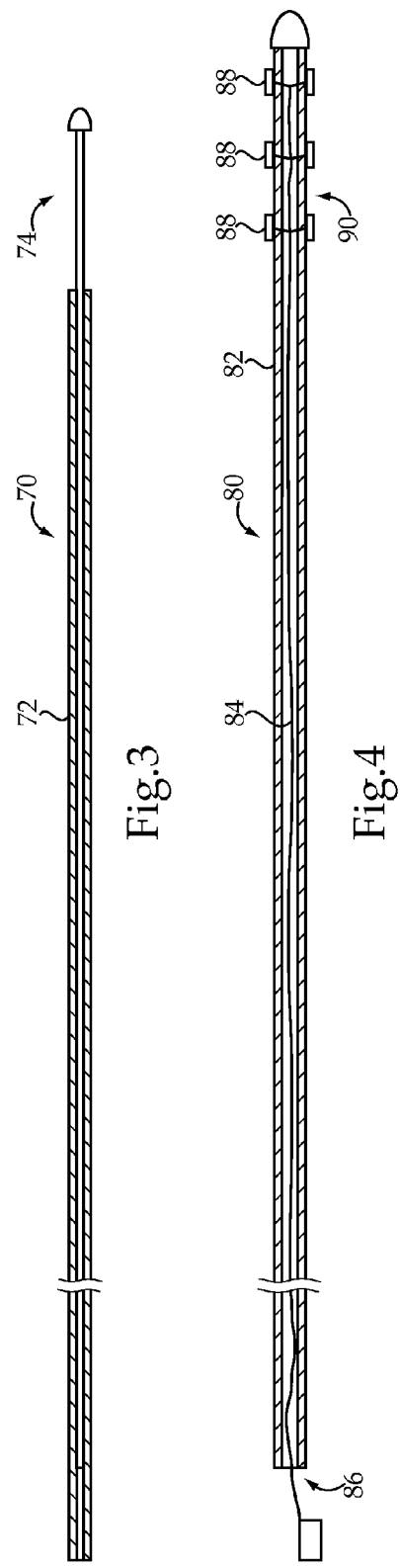
Fig.1
Fig.2
Fig.3
Fig.4

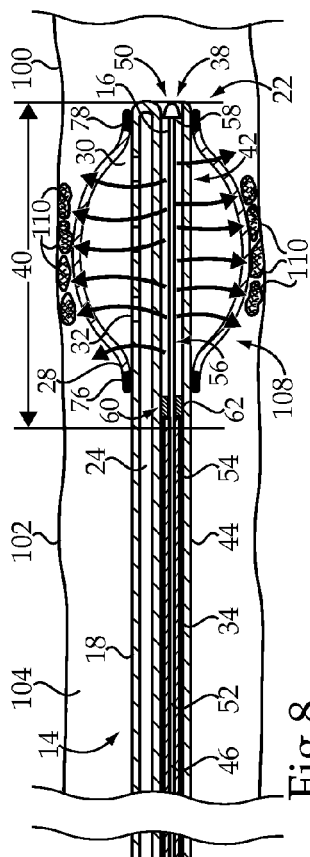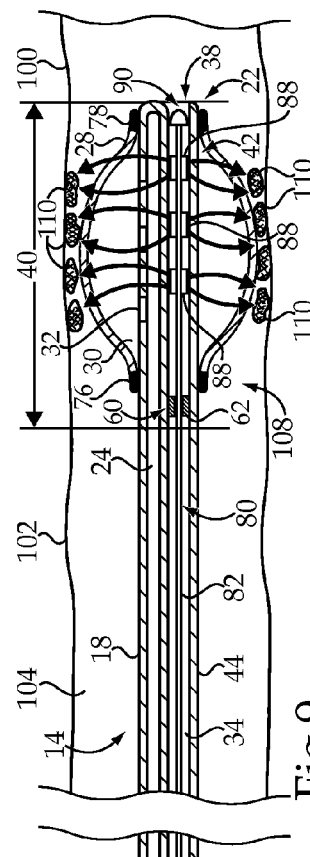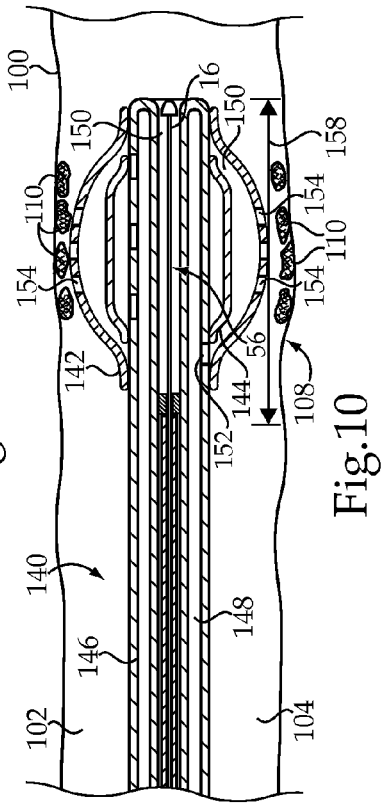

INTRALUMINAL ACTIVATION SYSTEM AND METHOD OF ACTIVATING AN INACTIVE AGENT

TECHNICAL FIELD

The present disclosure relates generally to an intraluminal activation system for activating an inactive agent, and more particularly to an intraluminal activation system including an elongate energy transmission wire configured for use with a balloon catheter.

BACKGROUND

Drugs, polymers, or other materials may have an inactive state, which can later be transitioned into an active state. For example, with respect to a chemotherapeutic agent, there may be a desire to deliver the chemotherapeutic agent in concentrated amounts directly to a treatment site to reduce systemic side effects. Further, depending on the treatment site, there may be a desire to deliver the chemotherapeutic agent in an inactive, or inert, state systemically and later activate the chemotherapeutic agent at the treatment site. Contemplated activation means for activating inactive agents, such as a chemotherapeutic agent, may include, for example, light energy, thermal energy, radiation, magnetic energy, or the use of a chemical reaction inducing agent. For example, light activated drugs, or photodynamic therapy, are currently being researched and developed.

U.S. Patent Application Publication No. 2009/0118816 to Kipshidze et al. (hereinafter Kipshidze) discloses a treatment system for providing energy therapy to a patient. The treatment system includes an implantable device and an activation system having a plurality of energy emitters that transmit energy towards the device. In particular, the implantable device may be a stent having an energy activated treatment agent thereon. The activation system includes a light emitting catheter configured to output light of the appropriate absorptive wavelength to activate the treatment agent. According to the disclosed embodiment, the light emitting catheter may include a light source array containing light emitting diodes disposed on conductive traces electrically connected to leads extending proximally through a lumen of the light emitting catheter to an external power supply and control device. Although the treatment system of Kipshidze may be useful for the disclosed application, it should be appreciated that there may be a need for new and improved intraluminal systems, particularly as the use of inactivate agents is further developed.

The present disclosure is directed toward one or more of the problems or issues set forth above.

SUMMARY OF THE DISCLOSURE

In one aspect, an intraluminal activation system for activating an inactive agent includes a catheter having an elongate tubular body defining an inflation lumen and a medical device lumen. A longitudinal segment of a distal end of the elongate tubular body defines a transparent treatment region. An inflation balloon is disposed at the distal end of the elongate tubular body and over at least a portion of the transparent treatment region. The inflation lumen is in fluid communication with an interior space of the inflation balloon. The intraluminal activation system also includes an elongate energy transmission wire configured to transmit activation energy from a proximal end of the elongate energy transmission wire to a distal end of the elongate energy transmission wire. The intraluminal activation system has an activation configuration in which the inflation balloon is expanded, the elongate energy transmission wire is telescopically received within the medical device lumen such that the distal end of the elongate energy transmission wire is within the transparent treatment region, and activation energy is emitted from the distal end of the elongate energy transmission wire, through the transparent treatment region, through the inflation balloon, and toward the inactive agent.

In another aspect, a method of activating an inactive agent using an intraluminal activation system is provided. The intraluminal activation system includes a catheter having an elongate tubular body defining an inflation lumen and a medical device lumen. A longitudinal segment of a distal end of the elongate tubular body defines a transparent treatment region. An inflation balloon is disposed at the distal end of the elongate tubular body and over at least a portion of the transparent treatment region. The inflation lumen is in fluid communication with an interior space of the inflation balloon. The intraluminal activation system also includes an elongate energy transmission wire configured to transmit activation energy from a proximal end of the elongate energy transmission wire to a distal end of the elongate energy transmission wire. The method includes steps of advancing the transparent treatment region of the catheter to a treatment site including the inactive agent and expanding the inflation balloon at the treatment site. The elongate energy transmission wire is then positioned within the medical device lumen of the catheter such that the distal end of the elongate energy transmission wire is within the transparent treatment region. The method also includes a step of emitting activation energy from the distal end of the elongate energy transmission wire, through the transparent treatment region, through the inflation balloon, and toward the inactive agent.

BRIEF DESCRIPTION OF THE DRAWINGS

FIG. 1 is a partially sectioned side diagrammatic view of an intraluminal activation system, according to one embodiment of the present disclosure;

FIG. 2 is a partially sectioned side diagrammatic view of an alternative elongate energy transmission wire having a retractable sheath and being configured for use with the intraluminal activation system of FIG. 1, with the retractable sheath shown in an extended state;

FIG. 3 is a partially sectioned side diagrammatic view of the elongate energy transmission wire of FIG. 2, with the retractable sheath shown in a retracted state;

FIG. 4 is a partially sectioned side diagrammatic view of an another alternative elongate energy transmission wire configured for use with the intraluminal activation system of FIG. 1;

FIG. 8 is a partially sectioned side diagrammatic view of the vascular structure at another stage of a procedure for activating an inactive agent using the intraluminal activations system of FIG. 1;

FIG. 9 is a partially sectioned side diagrammatic view of the vascular structure at an alternative stage of a procedure for activating an inactive agent using the system disclosed herein; and FIG. 10 is a partially sectioned side diagrammatic view of the vascular structure at an alternative stage of a procedure for activating an inactive agent using an alternative embodiment of the system disclosed herein.

DETAILED DESCRIPTION

Figure 5:
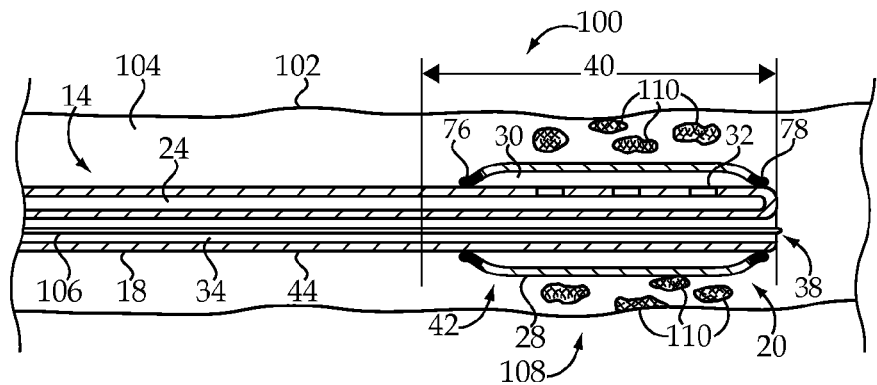
FIG. 5 is a partially sectioned side diagrammatic view of a vascular structure of a patient depicting one stage of a procedure for activating an inactive agent using the intraluminal activation system of FIG. 1.

Referring to FIG. 1, there is shown an intraluminal activation system 10 for activating an inactive agent according to one embodiment of the present disclosure. The intraluminal activation system 10 may include a number of components, which may be provided within a sterile, tear open package 12, as is known in the art. In performing an activation procedure on a patient, the components of the intraluminal activation system 10 and additional components may be used, depending upon the specifics of the procedure to be performed. As should be appreciated, however, components of the intraluminal activation system 10 might be separately packaged and/or the intraluminal activation system 10 might also include components in addition to those shown, including components routinely used in percutaneous vascular procedures.

In general, the intraluminal activation system 10 includes a catheter 14 and an elongate energy transmission wire 16. The catheter 14 may include an elongate tubular body 18 having a proximal end 20 and a distal end 22. The elongate tubular body 18 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular body 18 may define an inflation lumen 24 extending from a first proximal opening 26 to a transparent inflation balloon 28 disposed, or mounted, at the distal end 22 of the elongate tubular body 18. The inflation lumen 24 may be in fluid communication with an interior space 30 of the inflation balloon 28 via openings 32 through the elongate tubular body 18. Thus, as should be appreciated, a fluid source may be used to inflate the inflation balloon 28 via the inflation lumen 24 and openings 32. When inflated, or expanded, the inflation balloon 28 may assist in properly positioning an inactive agent within a lumen, such as a vascular lumen, and reducing fluid interference with respect to the transmission of activation energy.

The elongate tubular body 18 may also define a medical device lumen 34 extending from a second proximal opening 36 to a distal opening 38. Alternatively, however, the medical device lumen 34 may terminate at a closed distal end of the elongate tubular body 18. The medical device lumen 34 may be configured for receipt of any known medical device, including, for example, a wire guide or a snare. According to a specific example, the medical device lumen 34 may be a wire guide lumen configured for receipt of a standard wire guide, which may have an outer diameter of approximately 0.035 inch. Of course, alternative medical devices and/or wire guides of alternative sizes may be received within the medical device lumen 34. Although two lumens (i.e., inflation lumen 24 and medical device lumen 34) are shown, it should be appreciated that the catheter 14 disclosed herein may include alternative numbers of lumens, such as, for example, one lumen or three lumens.

According to the exemplary embodiment, a longitudinal, or axial, segment 40 of the elongate tubular body 18, at the distal end 22 thereof, is transparent and defines a transparent treatment region 42. The transparent treatment region 42 may be of any desired length and may permit the transmission of visible light, or other light energy, through walls 44 defining the elongate tubular body 18. The transparent treatment region 42, which includes transparent walls 44, may extend entirely about the elongate tubular body 18 such that a 360° treatment area surrounding the catheter 14 at the transparent treatment region 42 is provided. The 360° treatment area may represent an area external to, or radially spaced from, the catheter 14 at the transparent treatment region 42 that receives light energy transmitted through the transparent treatment region 42 from an interior space of the catheter 14, such as, for example, the medical device lumen 34. As used herein, "transparent" means to allow light to pass through. Thus, the "transparent" portions of the inflation balloon 28 and the catheter 14 should allow an amount of light sufficient to activate a particular inactive agent to pass therethrough. It may or may not be necessary for those transparent regions to be clear.

According to some embodiments, the inflation balloon 28, which is also transparent or substantially transparent, may include an opaque proximal segment 76 and an opaque distal segment 78. The opaque segments 76 and 78, which may be provided at conical ends of the inflation balloon 28 and thus may have conical shapes, may restrict the transmission of visible light at opposing ends of the inflation balloon 28. Such a modification may be desirable to limit an axial length of the circumferential treatment area and more precisely focus transmission of light activation energy.

The intraluminal activation system 10 also includes the elongate energy transmission wire 16 having an elongate body 46 configured to transmit activation energy from a proximal end 48 of the elongate energy transmission wire 16 to a distal end 50 of the elongate energy transmission wire 16. The elongate energy transmission wire 16 may have alternative configurations depending on the type of activation energy being transmitted. For example, according to the embodiment of FIG. 1, the elongate energy transmission wire 16 may include an optical fiber 52 for transmitting energy from various sources, such as, for example, light sources including a laser light source or many visible light sources. According to some embodiments, and as shown, a sheath 54, such as a protective sheath, may be positioned over a majority of a length of the optical fiber 52 and may terminate proximal to a distal energy emitting region 56 of the elongate energy transmission wire 16. Although not required, the distal energy emitting region 56 may correspond in axial length to the transparent treatment region 42 of the catheter 14.

The elongate energy transmission wire 16 may include an expanded distal tip 58. In particular, an outer diameter $d_1$ of the expanded distal tip 58 may correspond substantially to an inner diameter $d_2$ of the medical device lumen 34 at the transparent treatment region 42. In addition, or alternatively, the elongate energy transmission wire 16 may include an increased diameter region 60 at or near a proximal end of the distal energy emitting region 56. The increased diameter region 60 may define an outer diameter $d_3$ that also corresponds substantially to the inner diameter $d_2$ of the medical device lumen 34. For example, a sealing member 62 may be positioned about the elongate energy transmission wire 16 and may define the increased diameter region 60. The expanded distal tip 58 and/or the increased diameter region 60 may function to restrict fluids, such as bodily fluids, from entering the space between the distal energy emitting region 56 and the transparent treatment region 42 and interfering with light transmission.

According to an alternative embodiment, shown in FIG. 2, an elongate energy transmission wire 70, which may be configured for use with the catheter 14 of FIG. 1, may include a retractable sheath 72. In particular, the retractable sheath 72 may have an extended position, which is depicted in FIG. 2, in which the retractable sheath 72 covers a distal segment 74 of the elongate energy transmission wire 70, and a retracted position, which is shown in FIG. 3, in which the retractable sheath 72 terminates proximal to the distal segment 74 of the elongate energy transmission wire 70. The distal segment 74 may correspond to the distal energy emitting region 56 of the elongate energy transmission wire 16 of FIG. 1 and, during a procedure, the retractable sheath 72 may be proximally retracted to expose the distal segment 74 when the distal segment 74 is positioned at the transparent treatment region 42 of the catheter 14. For example, it may be desirable to expose the distal energy emitting region 56, described above, only when the elongate energy transmission wire 70 is properly positioned.

Turning now to FIG. 4, another alternative elongate energy transmission wire 80 is shown and may include a hollow tubular body 82. The hollow tubular body 82 may house one or more energy transmission wires 84 extending from an open proximal end 86 of the hollow tubular body 82 to a plurality of light emitting devices, such as light-emitting diodes, 88 positioned along a distal end 90 of the hollow tubular body 82. Various other light sources, including natural and artificial light sources, may be transmitted using the intraluminal activation system 10 described herein. In addition, the intraluminal activation system 10 of the present disclosure may be adapted to deliver various other forms of activation energy, depending on the energy form required to activate a particular inactive agent.

INDUSTRIAL APPLICABILITY

Turning now to FIG. 5, a percutaneous vascular procedure using the intraluminal activation system 10 of FIG. 1 will be discussed with reference to a vascular structure 100 of a patient. Although a vascular structure 100 is shown, the present disclosure may be applicable to alternative bodily structures and lumens. The vascular structure 100, as should be appreciated, may include a vessel wall 102 defining a lumen 104. Although not shown, it should be appreciated that a clinician may first use an introducer to gain access to the vascular structure 100 in a known manner. Next, as shown in FIG. 5, the catheter 14 may be inserted through the introducer, over a standard wire guide 106, and into the vascular structure 100. The catheter 14 may be advanced such that the transparent treatment region 42 of the catheter 14 is positioned at a treatment site 108 that includes an inactive agent 110.

An exemplary inactive agent 110 may include a drug that may be delivered to the treatment site 108 and remain inert until activated by light energy. The inactive agent 110 may be delivered using various known means, including delivery by a catheter, such as catheter 14, balloon, wire, sheath, cartridge, or the like. According to some examples, the inactive agent 110 may be supported on a prosthetic implant, such as a stent, graft, filter, or the like. Additional devices and structures may be used to deliver, support, and/or contain the inactive agent 110 with respect to the target site 108.

Figure 6:
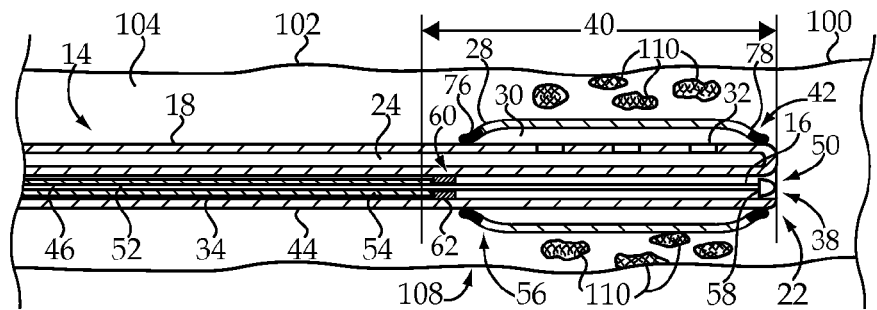
FIG. 6 is a partially sectioned side diagrammatic view of the vascular structure at an alternative stage of a procedure for activating an inactive agent using the intraluminal activation system of FIG. 1.

The standard wire guide 106 may be removed and, at a next stage of the procedure shown in FIG. 6, the elongate energy transmission wire 16 may be positioned within the medical device lumen 34 of the catheter 14. In particular, the elongate energy transmission wire 16 may be advanced through the medical device lumen 34 such that the distal end 50 or, more particularly, the distal energy emitting region 56 of the elongate energy transmission wire 16 is positioned within, or otherwise substantially aligned with, the transparent treatment region 42. Alternatively, the elongate energy transmission wire 16 may be used in place of the standard wire guide 106 to gain access to the treatment site 108. As such, the medical device lumen 34 of the catheter 14 may be advanced over the elongate energy transmission wire 16 and advanced to the treatment site 108.

Figure 7:
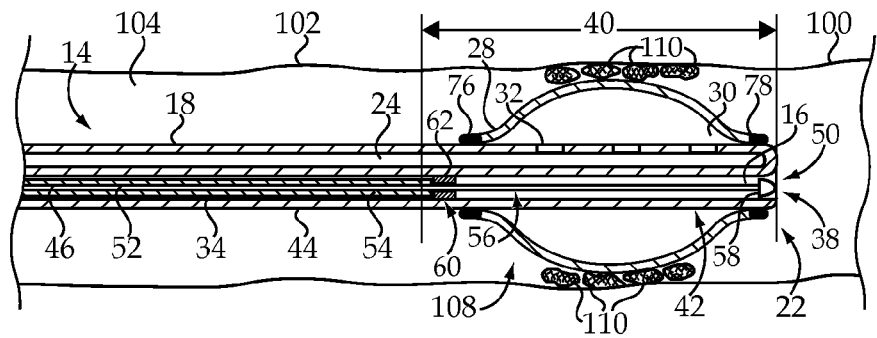
FIG. 7 is a partially sectioned side diagrammatic view of the vascular structure at another stage of a procedure for activating an inactive agent using the intraluminal activation system of FIG. 1.

Next, as shown in FIG. 7, the inflation balloon 28 may be expanded at the treatment site 108. For example, a fluid source may be used to inflate the inflation balloon 28 via the inflation lumen 24 and openings 32 discussed above. As the inflation balloon 28 is expanded, the inactive agent 110 may be pressed or held against the vessel wall 102. Further, an expanded state of the inflation balloon 28 may reduce fluid interference, such as by bodily fluids, between the distal end 50 of the elongate energy transmission wire 16 and the inactive agent 110.

Activation energy may be emitted from the distal end 50, or distal energy emitting region 56, of the energy transmission wire 16, through the transparent treatment region 42, through the transparent inflation balloon 28, and toward the inactive agent 110, as shown in FIG. 8. In particular, FIG. 8 depicts an activation configuration of the intraluminal activation system 10 in which the inflation balloon 28 is expanded, the elongate energy transmission wire 16 is telescopically received within the medical device lumen 34 such that the distal end 50 of the elongate energy transmission wire 16 is within the transparent treatment region 42, and activation energy is emitted from the distal energy emitting region 56 of the elongate energy transmission wire 16, through the transparent treatment region 42, through the inflation balloon 28, and toward the inactive agent 110. According to some embodiments, transmission of activation light energy may be restricted by opaque segments 76 and 78 of the inflation balloon 28.

As stated above, the elongate energy transmission wire 16 may be an optical fiber 52 configured to emit light energy from the distal energy emitting region 56 toward the inactive agent 110. Although no outer sheath is required, the exemplary embodiment depicts a sheath 54 that terminates proximal to a distal energy emitting region 56 of the elongate energy transmission wire 16. If an elongate energy transmission wire 70 including a retractable sheath 72, as shown in FIG. 2, is used, the retractable sheath 72 may be proximally retracted to expose the distal segment 74 when the distal segment 74 is positioned at the transparent treatment region 42 of the catheter 14.

According to some embodiments, a light collector 120, or other similar device, may be positioned at the proximal end 20 of the optical fiber 52 to optimize the amount of ambient light collected and transmitted to the inactive agent 110. Alternatively, or additionally, optical filters located on the surface of the optical fiber 52, either proximally or distally, might optimize the activation of the inactive agent 110, depending on the wavelength sensitivity. It should be appreciated that various light sources or devices for providing or improving light energy may be substituted for the light collector 120.

As shown in FIG. 9, and according to the alternative elongate energy transmission wire 80 of FIG. 4, light energy may alternatively be emitted from the plurality of light emitting devices, or light-emitting diodes, 88 positioned along the distal end 90 of the hollow tubular body 82. According to such embodiments, the hollow tubular body 82 of the alternative elongate energy transmission wire 80 may house one or more energy transmission wires 84 extending from an open proximal end 86 of the hollow tubular body 82 to the plurality of light emitting devices 88. For example, a power source 130 may provide power to the plurality of light emitting devices 88 along the energy transmission wires 84.

Referring again to FIG. 8, bodily fluids within the medical device lumen 34 may be removed, or prevented from interfering with, the transparent treatment region 42 during positioning of the elongate energy transmission wire 16 with respect to the catheter 14 using the expanded distal tip 58 and the increased diameter region 60.

According to an alternative embodiment shown in FIG. 10, a catheter 140 including a transparent outer weeping balloon 142 for delivering the inactive agent 110 may be used with the teachings of the present disclosure. For example, the catheter 140 may include a transparent inner inflation balloon 144 in fluid communication with an inflation lumen 146 of the catheter 140. An infusion lumen 148 of the catheter 140 may be in fluid communication with an interior 150 of the outer weeping balloon 142 via openings 152 for delivering the inactive agent 110. The outer weeping balloon 142 may include openings 154 for releasing the inactive agent 110 provided through the infusion lumen 148 at the target site 108. The inactive agent 110 may be released at any level of expansion of the inner inflation balloon 144.

The elongate energy transmission wire 16 described herein may be used with the catheter 140 of FIG. 10 to effect activation of the inactive agent 110 during and/or after release of the inactive agent 110 into the lumen 104. As described above, the elongate energy transmission wire 16 may be inserted through a medical device lumen 156 of the catheter 140 or the medical device lumen 156 of the catheter 140 may be advanced over the elongate energy transmission wire 16. Ultimately, the inner inflation balloon 144 may be expanded, the elongate energy transmission wire 16 may be positioned such that the distal energy emitting region 56 is within a transparent treatment region 158 of the catheter 140, and activation energy, such as light energy, is emitted from the distal energy emitting region 56 of the elongate energy transmission wire 16, through the transparent treatment region 158, through the inner inflation balloon 144, through the outer weeping balloon 142, and toward the inactive agent 110.

The intraluminal activation system 10 of the present disclosure includes a minimally invasive means for activating an inactive agent 110. In particular, the elongate energy transmission wire 16, 70, 80 of the present disclosure may have a size similar to standard wire guides and, thus, may be positioned through medical device lumens sized for receiving standard wire guides. As a result, catheters, such as catheters 14 and 140, designed for use with the elongate energy transmission wire 16, 70, 80 may not require a separate, additional lumen sized and configured specifically for receipt of an energy transmission device. Also provided herein are means, such as balloons 28 and 144 and regions 58 and 60, for reducing fluid interference, particularly with respect to the transmission of light energy, at the target site 108. The distal energy emitting region 56, transparent treatment region 42, 158 and transparent balloons 28, 144, 142 facilitate the directed transmission of activation energy, such as light energy, toward a circumferentially symmetrical activation area.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. An intraluminal activation system for activating an inactive agent, comprising:
   a catheter having an elongate tubular body defining an inflation lumen and a medical device lumen, wherein a longitudinal segment of a distal end of the elongate tubular body defines a transparent treatment region;
   an inflation balloon disposed at the distal end of the elongate tubular body and over at least a portion of the transparent treatment region, wherein the inflation lumen is in fluid communication with an interior space of the inflation balloon; and
   an elongate energy transmission wire configured to transmit activation energy from a proximal end of the elongate energy transmission wire to a distal end of the elongate energy transmission wire;
   wherein the intraluminal activation system has an activation configuration in which the inflation balloon is expanded, the elongate energy transmission wire is telescopically received within the medical device lumen such that the distal end of the elongate energy transmission wire is within the transparent treatment region, and activation energy is emitted from the distal end of the elongate energy transmission wire, through the transparent treatment region, through the inflation balloon, and toward the inactive agent.

2. The intraluminal activation system of claim 1, wherein the elongate energy transmission wire includes an optical fiber; and
   the intraluminal activation system has an inactive configuration in which the distal end of the elongate energy transmission wire is outside of the transparent treatment region.

3. The intraluminal activation system of claim 2, further including a sheath positioned over a majority of a length of the optical fiber and terminating proximal to the distal end of the elongate energy transmission wire.

4. The intraluminal activation system of claim 2, further including a retractable sheath positioned over the optical fiber, wherein the retractable sheath has an extended position in which the retractable sheath covers the distal end of the elongate energy transmission wire and a retracted position in which the retractable sheath terminates proximal to the distal end of the elongate energy transmission wire.

5. The intraluminal activation system of claim 1, wherein the medical device lumen terminates at a distal opening of the elongate tubular body.

6. The intraluminal activation system of claim 5, wherein the elongate energy transmission wire includes an expanded distal tip, wherein an outer diameter of the expanded distal tip corresponds to an inner diameter of the medical device lumen at the transparent treatment region.

7. The intraluminal activation system of claim 5, wherein the elongate energy transmission wire includes an increased diameter region at a proximal end of the transparent treatment region, wherein the increased diameter region corresponds to an inner diameter of the medical device lumen at the transparent treatment region.

8. The intraluminal activation system of claim 7, further including a sealing member positioned about the elongate energy transmission wire and defining the increased diameter region.

9. The intraluminal activation system of claim 1, wherein the elongate energy transmission wire is hollow and houses energy transmission wires extending from an open proximal end of the elongate energy transmission wire to a plurality of light emitting devices positioned along the distal end of the elongate energy transmission wire.

10. The intraluminal activation system of claim 1, wherein the inflation balloon is a transparent inflation balloon having a proximal opaque segment and a distal opaque segment.

11. The intraluminal activation system of claim 1, wherein the elongate tubular body further defines an infusion lumen in fluid communication with an outer weeping balloon, wherein the infusion lumen and the outer weeping balloon are configured for delivery of the inactive agent.

12. A method of activating an inactive agent using an intraluminal activation system, the intraluminal activation system including a catheter having an elongate tubular body defining an inflation lumen and a medical device lumen, wherein a longitudinal segment of a distal end of the elongate tubular body defines a transparent treatment region, an inflation balloon disposed at the distal end of the elongate tubular body and over at least a portion of the transparent treatment region, wherein the inflation lumen is in fluid communication with an interior space of the inflation balloon, and an elongate energy transmission wire configured to transmit activation energy from a proximal end of the elongate energy transmission wire to a distal end of the elongate energy transmission wire, the method comprising steps of:

advancing the transparent treatment region of the catheter to a treatment site including the inactive agent;

expanding the inflation balloon at the treatment site;

advancing the elongate energy transmission wire within the medical device lumen of the catheter to a position at which the distal end of the elongate energy transmission wire is within the transparent treatment region; and emitting activation energy from the distal end of the elongate energy transmission wire, through the transparent treatment region, through the inflation balloon, and toward the inactive agent.

13. The method of claim 12, wherein the expanding step includes pressing the inactive agent against lumen walls.

14. The method of claim 12, wherein the expanding step includes reducing fluid interference between the distal end of the elongate energy transmission wire and the inactive agent.

15. The method of claim 12, wherein the advancing step includes advancing the medical device lumen of the catheter over the elongate energy transmission wire.

16. The method of claim 12, further including:

advancing the medical device lumen of the catheter over a wire guide and to the treatment site;

removing the wire guide from the medical device lumen; and advancing the elongate energy transmission wire through the medical device lumen after the wire guide has been removed.

17. The method of claim 12, wherein the elongate energy transmission wire is an optical fiber and the emitting step includes emitting light energy from the optical fiber.

18. The method of claim 12, further including retracting a retractable sheath positioned over the elongate energy transmission wire to expose the distal end of the elongate energy transmission wire after the positioning step.

19. The method of claim 12, wherein the emitting step includes emitting light energy from a plurality of light emitting devices positioned spaced longitudinally apart from each other along the distal end of the elongate energy transmission wire.

20. The method of claim 19, further including housing energy transmission wires that provide power to the plurality of light emitting devices within a hollow body of the elongate energy transmission wire.

* * * * *